(12) United States Patent
Kilibarda et al.

(10) Patent No.: US 9,410,895 B2
(45) Date of Patent: Aug. 9, 2016

(54) PROCESS AND APPARATUS FOR INSPECTING A HIGH VOLUME MATERIAL JOINTING OPERATION

(71) Applicant: Comau, Inc, Southfield, MI (US)

(72) Inventors: Velibor Kilibarda, West Bloomfield, MI (US); He Wang, Southfield, MI (US); Martin Kinsella, Southfield, MI (US)

(73) Assignee: Comau LLC, Southfield, MI (US)

( * ) Notice: Subject to any disclaimer, the term of this patent is extended or adjusted under 35 U.S.C. 154(b) by 77 days.

(21) Appl. No.: 14/206,246

(22) Filed: Mar. 12, 2014

(65) Prior Publication Data

US 2014/0259600 A1    Sep. 18, 2014

Related U.S. Application Data

(60) Provisional application No. 61/778,481, filed on Mar. 13, 2013.

(51) Int. Cl.
| | |
|---|---|
| *G01B 11/06* | (2006.01) |
| *G01N 21/84* | (2006.01) |
| *G01B 11/25* | (2006.01) |
| *G01N 21/95* | (2006.01) |
| *B21J 15/02* | (2006.01) |

(Continued)

(52) U.S. Cl.
CPC ............... *G01N 21/84* (2013.01); *B21J 15/025* (2013.01); *B21J 15/28* (2013.01); *B23K 31/125* (2013.01); *G01B 11/25* (2013.01); *G01N 21/9515* (2013.01); *B23P 19/06* (2013.01); *Y10T 29/49769* (2015.01); *Y10T 29/49947* (2015.01); *Y10T 29/53078* (2015.01)

(58) Field of Classification Search
CPC . G01N 21/84; G01N 21/9515; B23K 31/125; B21J 15/025; B21J 15/28; G01B 11/25; G01L 5/00; Y10T 29/53078; Y10T 29/49947; Y10T 29/49769; Y10T 29/53087; Y10T 29/5343; Y10T 29/49764; B23P 19/06
See application file for complete search history.

(56) References Cited

U.S. PATENT DOCUMENTS 5,691,815 A * 11/1997 Huber ................ G01B 11/0608
                                                                  250/559.19
5,741,096 A    4/1998 Olds
(Continued)

OTHER PUBLICATIONS

Notification of Transmittal of the International Search Report and the Written Opinion of the International Searching Authority, or the Declaration, dated Jul. 11, 2014.

(Continued)

*Primary Examiner* — David Bryant
*Assistant Examiner* — Jun Yoo
(74) *Attorney, Agent, or Firm* — Young Basile Hanlon & MacFarlane, P.C.

(57) ABSTRACT

A method of sequentially performing a plurality of jointing operations includes positioning an automated device to form a mechanical joint into a workpiece and forming a mechanical joint into the workpiece. Once the mechanical joint is formed, the workpiece is scanned to generate data indicating the surface geometry of the workpiece at a location including the mechanical joint. One or more geometric features of the surface geometry are identified, and if the identified geometric features are within respective predetermined specification thresholds, the automated device is repositioned to form a subsequent mechanical joint into the workpiece.

16 Claims, 7 Drawing Sheets

(51) Int. Cl.
   *B21J 15/28* (2006.01)
   *B23K 31/12* (2006.01)
   *B23P 19/06* (2006.01)

(56) References Cited

U.S. PATENT DOCUMENTS 7,123,982 B2   10/2006   Mauer et al.
7,423,734 B1 *  9/2008   Luik ..................... B23B 31/00
                                                            356/141.1
2012/0234805 A1   9/2012   Schwarz
2015/0101175 A1 * 4/2015   Xi ........................ B21J 15/025
                                                            29/525.06

OTHER PUBLICATIONS

LMI Technologies Inc., Gocator 2000 Series Data Sheet.

* cited by examiner

ESTIMATED TIME FOR INSPECTION

| STEPS | INDIVIDUAL TIME(S) | TOTAL TIME(S) |
|---|---|---|
| 1. AUTOMATED DEVICE IN POSITION | | 0.10-0.65 |
| 2. PERFORM JOINTING | | |
| 3. TRIGGER SENSOR | 0.02-0.15 | |
| 4. PROCESS DATA | 0.05-0.2 | |
| 5. REPORT DATA | 0.03-0.3 | |
| 6. AUTOMATED DEVICE MOVES TO NEXT JOINT POINT/ RETRY | | |

PROCESS AND APPARATUS FOR INSPECTING A HIGH VOLUME MATERIAL JOINTING OPERATION

CROSS REFERENCE TO RELATED APPLICATION

This application claims priority benefit to U.S. Provisional Patent Application No. 61/778,481 filed Mar. 13, 2013, which is incorporated herein by reference in its entirety.

TECHNICAL FIELD

The embodiments disclosed herein generally relate to inspection of a material jointing operation in which a mechanical joint is used to join two or more pieces of material.

BACKGROUND

Mechanical joints are often used to join two or more pieces of material, for example sheets of metal, in a variety of jointing operations. Mechanical joints can be formed, for instance, in high volume automated jointing operations involving the sequential formation of a large number of mechanical joints. In these jointing operations, the inspection of the mechanical joints, if any, is typically performed by a human operator on a random sampling of the formed mechanical joints.

SUMMARY

The embodiments described herein relate to the inspection of a high volume jointing operation. In one aspect, an apparatus for performing a jointing operation includes an automated device configured for forming a mechanical joint into a workpiece. A sensor is coupled to the automated device in order to scan the workpiece and generate data indicating the surface geometry of the workpiece at a location including a mechanical joint formed by the automated device. A system controller is programmed to identify one or more geometric features of the surface geometry that indicate the quality of the mechanical joint. If the identified geometric features are within respective predetermined specification thresholds, the controller will reposition the automated device to form a subsequent mechanical joint into the workpiece.

In one example, the automated device is configured to drive a self-piercing rivet or other fastener through the workpiece to form the mechanical joint. Based on the input from the sensor, the controller can be configured to identify the presence, height or location of a head of the fastener.

These and other aspects will be described in additional detail below.

BRIEF DESCRIPTION OF THE DRAWINGS

The various features, advantages and other uses of the present apparatus will become more apparent by referring to the following detailed description and drawings in which.

DETAILED DESCRIPTION

Mechanical joints are often used to join two or more pieces of material, such as sheets of metal, in a workpiece. The formation of a mechanical joint into a workpiece can alter the surface geometry of one or more of the joined pieces of material. For instance, in the example of FIGS. 1A and 1B, a workpiece W includes a mechanical joint 10 formed between two pieces of sheet metal material 12 and 14 by a self-piercing rivet 16. As shown, a head 18 of the rivet 16 projects from a surface 20 of the workpiece W defined by the upper piece of material 12 and extends a height H beyond the surface 20 at a nominal joint location 22. Similarly, in the example of FIGS. 2A and 2B, for a workpiece W including a mechanical joint 30 formed through two pieces of material 32 and 34 by a threaded fastener 36, a hex-head 38 of the threaded fastener 36 projects from a surface 40 of the workpiece W defined by the upper piece of material 32 and extends a height H beyond the surface 40 at a nominal joint location 42.

Figure 1A:
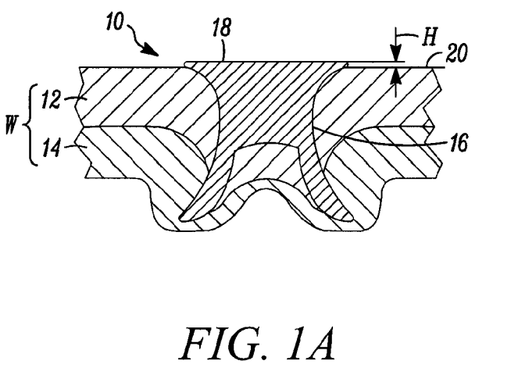
FIG. 1A is a cross sectional view of a workpiece in which an example of a mechanical joint is formed between two pieces of material with a self-piercing rivet.
Figure 1B:
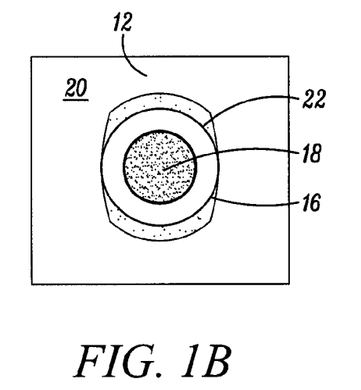
FIG. 1B is a top view of the workpiece of FIG. 1A.
Figure 2A:
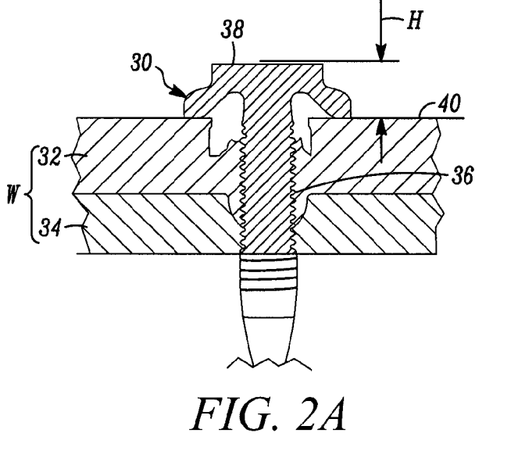
FIG. 2A is a cross sectional view of a workpiece in which another example of a mechanical joint is formed with a threaded fastener.
Figure 2B:
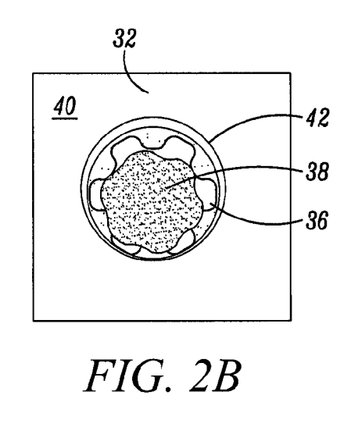
FIG. 2B is a top view of the workpiece of FIG. 2A.

As can be seen from these non-limiting examples, mechanical joints may be formed in a jointing operation using self-piercing rivets 16 or using threaded fasteners 36, for instance. Mechanical joints can also be formed in a variety of other types of jointing operations, including without limitation stud weld jointing operations, clinch jointing operations, weld nut jointing operations, self-piercing stud jointing operations, pierce nut jointing operations and spot welding jointing operations. Although the description that follows proceeds with reference to certain illustrated examples of jointing operations and resulting mechanical joints, it will be understood that the principles of this disclosure are equally applicable to mechanical joints formed using any of the foregoing or other jointing operations known by those skilled in the art.

The surface geometry of a workpiece at a location including a mechanical joint may reflect one or more qualities or other characteristics of the mechanical joint. The surface geometry may reflect, for example, the presence of a mechanical joint, the height of a mechanical joint and/or the positional location of a mechanical joint in relation to a nominal joint location.

Figure 3:
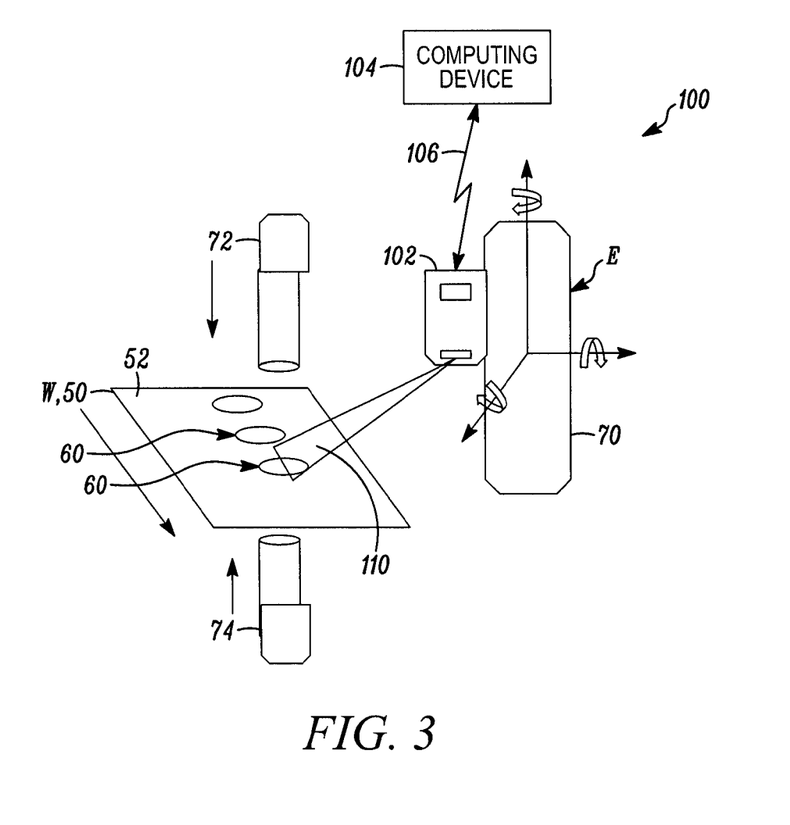
FIG. 3 is a schematic representation of an example of a system for sequentially forming mechanical joints in a workpiece and for determining the quality and integrity of the mechanical joints.

An example system 100 for inspecting a workpiece to acquire data indicating its surface geometry at a location including a mechanical joint, and for analyzing the data to identify one or more qualities or other characteristics of the mechanical joint, is shown in FIG. 3. As will be appreciated from the description that follows, the system 100 supports in-process or post-process inspection of the formation of mechanical joints used to join two or more pieces of material in a jointing operation. This ability, among other things, provides an opportunity for improved quality control over the formation of individual mechanical joints and over the jointing operation as a whole.

The system 100 can, by providing for relatively short control loops, identify a substandard or potentially defective mechanical joint right after the mechanical joint is formed, for example. This information can be used in-process to adjust a joining operation and greatly reduce or eliminate subsequent substandard or defective mechanical joints. The system 100 may be used in an exemplary application to support the coordinated operation of automated equipment used to sequentially form large numbers of mechanical joints into one or more workpieces.

The system 100 is illustrated and explained with reference to an exemplary workpiece W. The workpiece W could be a portion of a vehicle body-in-white (BIW), for instance. The workpiece W has an upper piece of material 50 and includes plurality of mechanical joints 60 formed between the upper piece of material 50 and an underlying piece of material (not shown). In the workpiece W, each of the mechanical joints 60 alters the geometry of a surface 52 of the workpiece W defined by the upper piece of material 50.

The mechanical joints 60 in this example may be formed in a jointing operation using self-piercing rivets, such as the self-piercing rivets 16 described above. The jointing operation, as shown, can be implemented with automated equipment E including an automated device configured to form the mechanical joint 60 into the workpiece W. In the illustrated example, the automated equipment E includes a programmable rivet gun 70. With the programmable rivet gun 70, a self-piercing rivet is forced through the workpiece 50 by the illustrated rivet punch 72 toward a rivet die 74 to form a mechanical joint 60 into the workpiece 50. The automated equipment E including the programmable rivet gun 70 can be configured to sequentially form a large number of mechanical joints 60 into the workpiece W. The structure and operation of one example of this equipment is described in U.S. patent application Ser. No. 14/173,298, which is assigned to the assignee of the present application and incorporated herein by reference in its entirety. However, as noted above, the principles of the system 100 are applicable to many other jointing operations known by those skilled in the art.

The system 100 generally includes a sensor 102 and a computing device 104. In this example, the sensor 102, as shown, may be mounted to the automated equipment E (e.g., for the illustrated example, automated equipment E including the programmable rivet gun 70) used to sequentially form large numbers of mechanical joints 60 into the workpiece W. The sensor 102 may be located remotely from the computing device 104, and communicatively coupled to the computing device 104 over a communications channel 106. The communication channel 106 is configured to allow for sharing of information, data and/or computing resources between the sensor 102 and the computing device 104. The communication channel 106 may be a wired or wireless channel, for example, using an industry standard or proprietary protocol. Alternatively, the sensor 102 and the computing device 106 could be integrated in a single device.

The sensor 102, the computing device 104 and optionally, other devices, may be configured with respective hardware and software so that, collectively, data indicating the surface geometry of the workpiece W at a location including a formed mechanical joint 60 can be acquired and analyzed to identify one or more quality or other characteristics of the mechanical joint 60. For the illustrated example, the data will indicate the geometry of the surface 52 of the workpiece W defined by the upper piece of material 50. It will be understood that the location including a formed mechanical joint 60 may be, or include, a predetermined nominal joint location according to a programmed routine of the automated equipment E.

In this example, the sensor 102 and the computing device 104 may each be one or multiple computers including a random access memory (RAM), a read-only memory (ROM) and a central processing unit (CPU) in addition to various input and output connections. Generally, the control functions described herein can be implemented by one or more software programs stored in internal or external memory and are performed by execution by the respective CPUs of the sensor 102 and the computing device 104. However, some or all of the functions could also be implemented by hardware components.

In the examples, the sensor 102 has at least one field of view 110. With the field of view 110 arranged to fall on the target area of an object, sensor 102 is generally configured to support the acquisition of data indicating the surface geometry of the objects at the target area. The sensor 102 may be, for example, a beam or sheet of light sensor including a laser diode and a CMOS detector configured to cast one or more lines of laser light across a target area and output data indicating the geometric features of an object in the target area. An exemplary sensor 102 of this type is a Gocator® sensor offered by LMI Technologies, Inc.

In the exemplary system 100, the sensor 102 is positionable to acquire data indicating the surface geometry of the workpiece W at respective predetermined nominal locations of the mechanical joints 60. The nominal joint location for a mechanical joint 60 formed into the workpiece W may include, for example, the protruding or upstanding head of a self-piercing rivet or a hex-head threaded fastener. In one example, the sensor 102 can be configured to cast one or more lines of laser light across a nominal location of a mechanical joint 60. According to this example, data can be acquired that indicates the geometry of a surface 52 of the workpiece W in respective two dimensional cross sectional planes transverse to the surface 52 of the workpiece W and extending though the nominal location of a mechanical joint 60.

The computing device 104 can analyze the acquired data in real-time to identify one or more quality or other characteristics of a mechanical joint 60 formed into the workpiece W. This identification can be made concerning, for example, the presence of a mechanical joint 60, the height of a mechanical joint 60 and/or the positional location of a mechanical joint 60 in relation to its nominal joint location. These or other aspects of the mechanical joint 60 can be quantified and compared to respective predetermined specification thresholds to determine whether the mechanical joint 60 meets its predetermined specification thresholds and passes inspection. The system 100 thus permits objective, automated inspection of the mechanical joint 60 without the need for resort to the subjectivity of human inspection.

Figure 4:
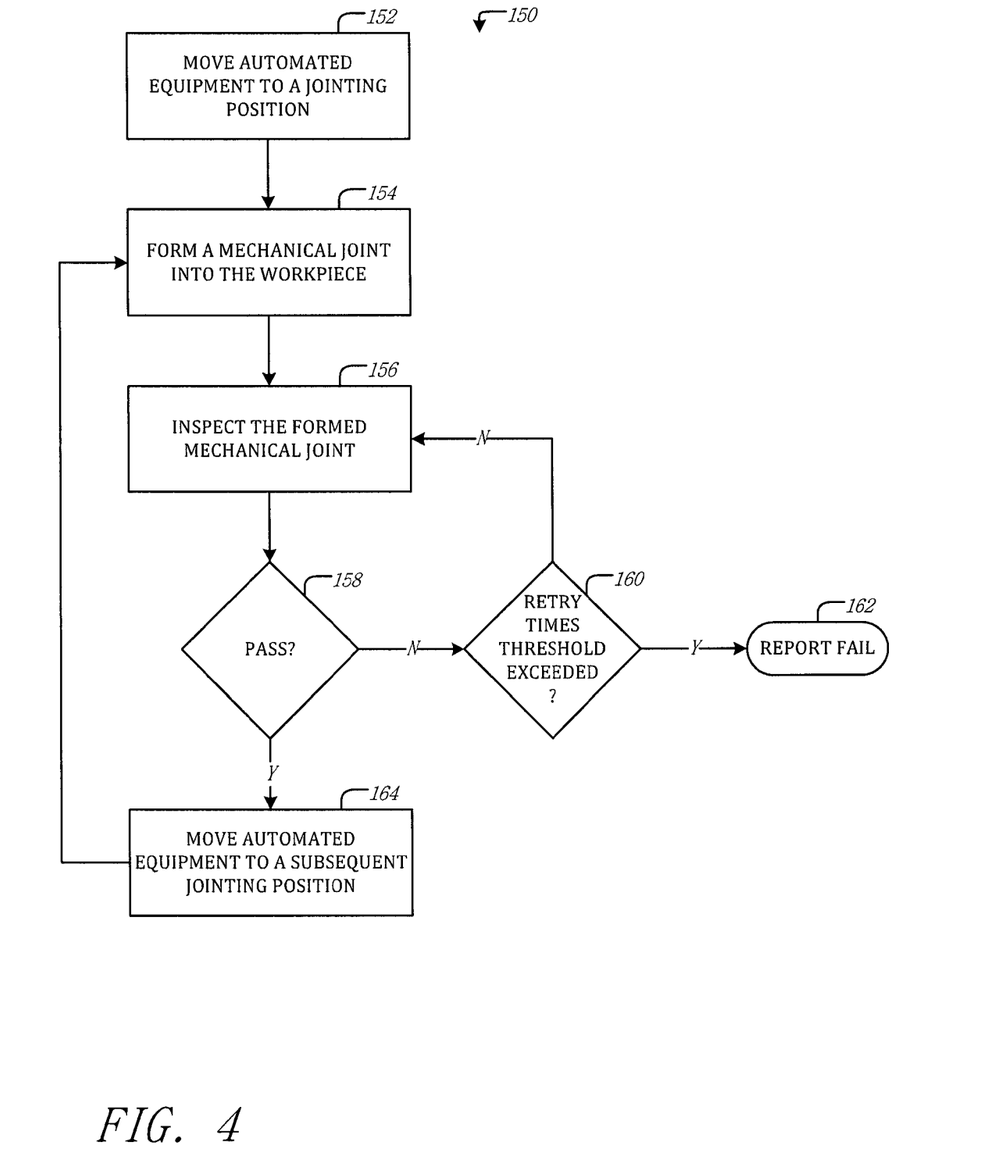
FIG. 4 is a flowchart depicting exemplary operations for performing an in-process inspection of the formation of a mechanical joint.

The operations of an illustrative in-process control routine 150 for coordinating the operation of the automated equipment E or other automated equipment used to sequentially form large numbers of mechanical joints 60 into one or more workpieces W are shown in FIG. 4. In exemplary operation 152, automated equipment, such as the automated equipment E including the programmable rivet gun 70, is moved to a jointing position. In the jointing position, the automated equipment E is operatively positioned, according to a programmed routine, to form a mechanical joint 60 into the workpiece W at a predetermined nominal joint location. In operation 154, the automated equipment E is controlled to perform a jointing operation in which a mechanical joint 60 is formed into the workpiece W.

In operation 156, after the joining operation is performed, the formed mechanical joint 60 is inspected. In the inspection, as generally described above, data indicating the surface geometry of the workpiece W at a location including the formed mechanical joint 60 is analyzed to identify one or more quality or other characteristics of the mechanical joint 60. This analysis can be performed in real-time in connection with a just formed mechanical joint 60 or at a later time.

Figure 5:
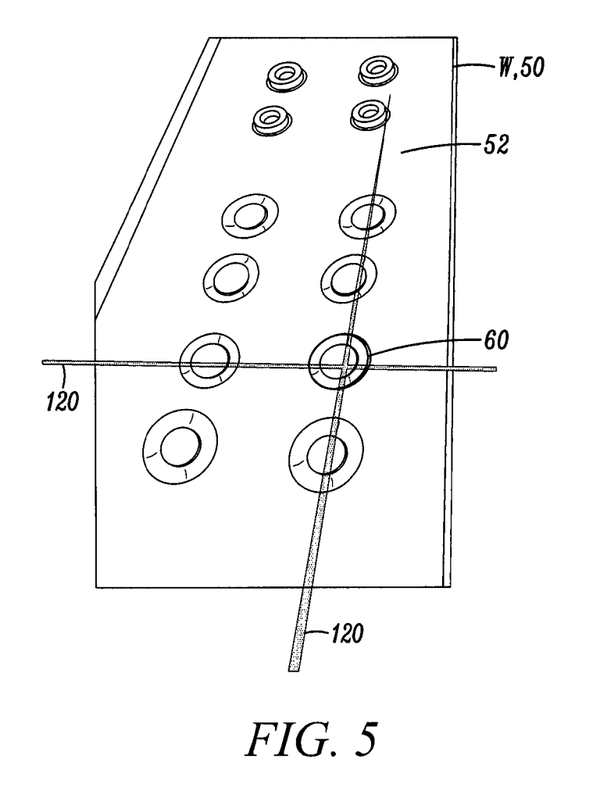
FIG. 5 is a perspective view of the surface of a workpiece that includes a mechanical joint, illustrating an aspect of acquiring data indicating the surface geometry of the workpiece at a location including the mechanical joint.

One example implementation of the inspection in operation 156 is explained with reference to FIG. 5. In this example, the acquired data indicates the geometry of the surface 52 of the workpiece W in two perpendicular two dimensional cross sectional planes transverse to the surface 52 of the workpiece W and extending though the nominal location of a mechanical joint 60. As shown, according to this example, two perpendicular lines of laser light 120 are projected across a target area including the nominal location of an illustrated mechanical joint 60. It will be understood, however, that additional and/or alternative beams could be used in connection with the acquisition of data indicating the geometry of the surface 52 of the workpiece W. The data in other examples, for instance, could indicate the geometry of a surface 52 of the workpiece W in a single two dimensional plane, or, data indicating the geometry of a surface 52 of the workpiece W in two parallel two dimensional planes. This or other data could alternatively and/or additionally be analyzed to identify one or more quality or other characteristics of the mechanical joint 60.

Examples of the analysis of the acquired data to identify one or more quality or other characteristics of the mechanical joint 60 are explained with reference to FIGS. 6A and 6B.

Figure 6A:
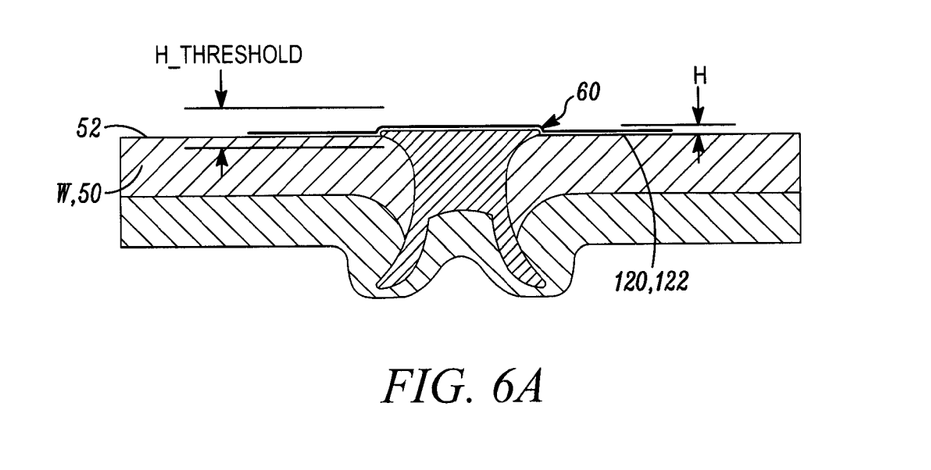
FIG. 6A is cross sectional view of the workpiece of FIG. 5 showing features of its surface geometry at the location including the mechanical joint.

According to the example, as indicated in FIG. 6A, the geometry of the surface 52 of the workpiece W is reflected by the geometric features of a shape or contour 122 of a line of a laser light 120 projected across the surface 52 and detected by the sensor 102. As indicated in FIG. 6A, data corresponding to the geometric features of the contour 122 can be used to quantify a joint height H. Specifically, the joint height H can be quantified as the difference between a height across the mechanical joint 60 and the height of the surrounding surface 52 of the workpiece W. The quantified joint height H can be compared to a predetermined specification threshold H_threshold for the height of the mechanical joint 60, for example, in identifying whether the mechanical joint 60 passes inspection. It will also be understood that, in this example, if the height H is quantified as substantially zero, it can be identified that a mechanical joint 60 is not present.

Figure 6B:
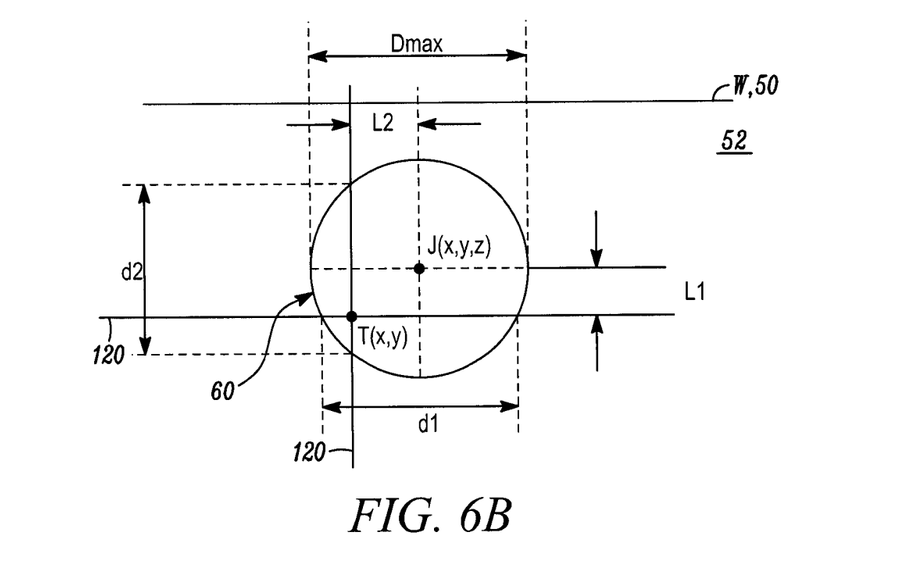
FIG. 6B is a schematic top view of the workpiece of FIG. 5 showing additional features of its surface geometry at the location including the mechanical joint.

As indicated in FIG. 6B, the location of the mechanical joint 60 can also be quantified from the data corresponding to the geometric features of the contour 122. In the illustrated example, D max is a known diameter of the top of the mechanical joint 60. D max may be, for instance, the diameter the head of a self-piercing rivet. As shown, the location of the mechanical joint 60 with respect to its nominal joint location is reflected by a difference between D max and lengths d1 and d2 of the contour 122. Specifically, with the lengths d1 and d2 of the contour 122 corresponding, respectively, to the lengths of the segment of the contour 122 that falls across the mechanical joint 60 for each of the lines of laser light 120, the difference between D max and lengths d1 and d2 of the contour 122 reflects the location of the mechanical joint 60 with respect to a nominal joint location T(x,y) for the mechanical joint 60.

According to this example, location deviation distances L1 and L2 from the nominal joint location T(x,y) for the mechanical joint 60 to the actual joint location of the mechanical joint 60 are given in Equations 1 and 2, respectively:

$$L1 = (D\text{max}/2)*\text{COS}(\text{ARCSIN}(d1/D\text{max}))$$ [Equation 1]

$$L2 = (D\text{max}/2)*\text{COS}(\text{ARCSIN}(d2/D\text{max}))$$ [Equation 2]

The quantified location deviation distances L1 and L2 from the nominal joint location can be compared to respective predetermined thresholds L1_threshold and L2_threshold for the location of the mechanical joint 60, for example, in identifying whether the mechanical joint 60 passes inspection.

In furtherance of the above described example, a location J(x,y,z) of the mechanical joint 60 can be determined using the quantified joint height H and the location deviation distances L1 and L2 from the nominal joint location T(x,y). In particular, it can be seen that Jx=Tx+L2, Jy=Ty+L1 and Jz=H.

Once identified, the height H, location deviation distances L1 and L2 from the nominal joint location and/or location J(x,y,z) of the mechanical joint 60 can be used individually or in any combination according to desired control logic to determine whether the quality, integrity or characteristics of the mechanical joint 60 meet respective predetermined specification thresholds and passes inspection. Although the illustrated example of the joint 60 has a circular topical geometry, it will be understood that similar data acquisition and analysis could be performed with respect to joints 60 with other geometries, such as polygonal geometries.

If the above described or other aspects of the inspection reveal that the mechanical joint 60 passes inspection in operation 158, only the one inspection is performed, and the control routine 150 repeats itself beginning at a subsequent iteration of operation 154, in which the automated equipment E is controlled to perform a subsequent jointing operation.

If, however, the inspection reveals that the mechanical joint 60 does not pass inspection in operation 158, the inspection can be retried in operation 160. If a threshold number of retry times has not been exceeded, in operation 160, the control routine 150 can return to operation 156 to retry the inspection of the mechanical joint 60. However, if a threshold number of retry times has been exceeded after the mechanical joint 60 does not pass inspection in operation 158, in operation 162, the control routine 150 reports a failure. After a failure is reported, the automated device E can cease inspection routines and the system 100 can be halted from forming additional mechanical joints 60 until the equipment E or process can be inspected.

It will be understood in connection with the forgoing description of the control routine 150 that additional and alternate operations may be performed, and that changes in order between the operations may be exist.

Figure 7:
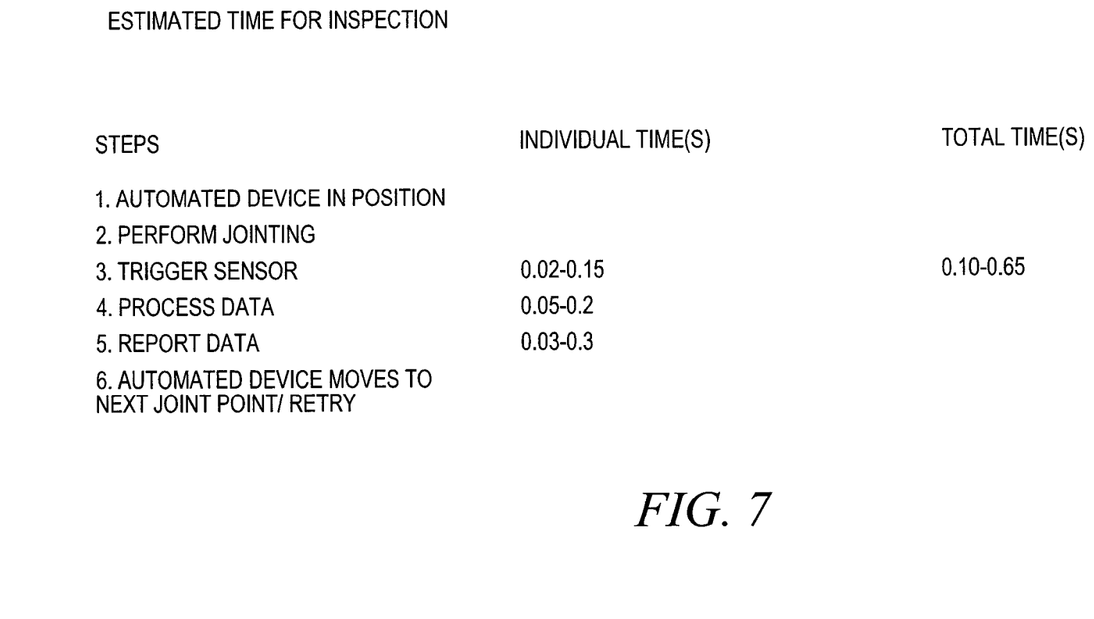
FIG. 7 is a table showing estimated times to perform certain of the operations for performing in-process inspection of the formation of the mechanical joints depicted in FIG. 4.

In FIG. 7, an exemplary table showing estimated times to perform the operations of the control routine 150, in accordance with the illustrated embodiment of the system 100, is presented. It can be seen that the system 100 provides for relatively short control loops and enables in-process inspection of mechanical joints 60 with no or little interruption to the functioning of the automated equipment E configured for forming the mechanical joints 60.

Additionally and/or alternatively to the above described in-process control, the system 100 could inspect a number of mechanical joints 60 after a certain set of mechanical joints 60 are formed. In these or other implementations of the system 100, information pertaining to a failure of a mechanical joint 60 can be used to minimize repair and/or to clear the automated equipment E used to form the substandard or potentially defective mechanical joint 60. The system 100 can also provide for acquisition and storage of data pertaining to a number of mechanical joints 60, which may be correlated to a time element and/or a product number, for example. These and other capabilities of the system 100 provide significant advantages over other inspection systems, such as manual inspection.

Figure 8A:
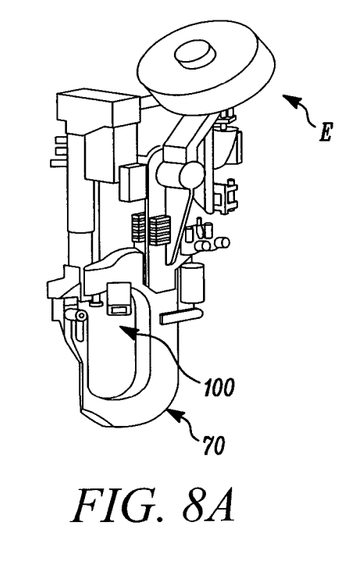
FIGS. 8A-C are schematic representations of the system of FIG. 3 implemented in connection with various exemplary equipment used to perform high volume jointing operations.
Figure 8B:
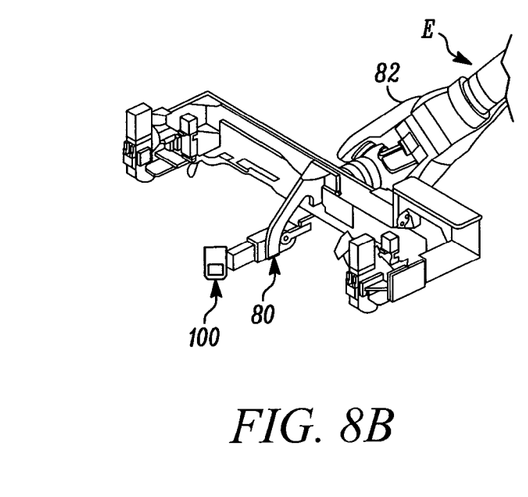
Figure 8C:
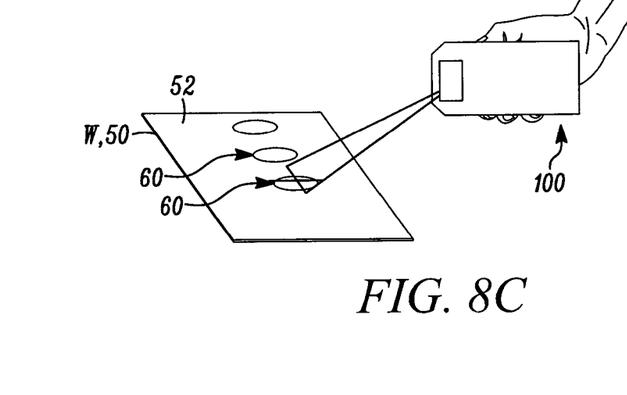

FIGS. 8A-C are schematic representations of the system 100 of FIG. 3 employed with, or applied to, various equipment. For instance, as shown in FIG. 8A, in furtherance to the illustrated example, the system 100 can be applied to the programmable rivet gun 70. In FIG. 8B, the system 100 is applied to an end effector 80 of an automated robot. In FIG. 8C, the system 100 is applied as a hand held system. In a hand held system, the sensor 102 for example, may be used with a support (not shown) which is manually positioned on the surface 50 of the workpiece W to project a beam and obtain real-time data in one or more of the manners described. Other hand held or portable systems known by those skilled in the art may be used.

While recited characteristics and conditions of the invention have been described in connection with certain embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for inspecting a jointing process, the method comprising the steps of:
   automatically scanning with a sensor connected to a programmable mechanical joint forming device a workpiece in an area including a formed mechanical joint;
   generating surface geometry data of the workpiece in the area including the formed mechanical joint;
   determining from the surface geometry data the positional X,Y location of the formed mechanical joint relative to the workpiece; and
   determining a coordinate positional X,Y locational variance between the determined formed mechanical joint positional X,Y location and a predetermined nominal positional X,Y location of the mechanical joint.

2. The method of inspecting of claim 1 wherein the step of scanning further comprises:
   projecting a light over the area including the formed mechanical joint;
   detecting a contour of the workpiece from the projected light, the detected contour defining the surface geometry data.

3. The method of inspecting of claim 2 wherein the step of projecting a light further comprises:
   projecting a line of laser light over the area including the formed mechanical joint, the laser light defining the detected contour.

4. The method of inspecting of claim 3 wherein the step of projecting a laser light comprises projecting a first and a second laser line light, the second laser line perpendicular to the first laser line light.

5. The method of inspecting of claim 4 wherein the step of determining the positional X,Y location of the formed mechanical joint further comprises the steps of:
   measuring a length of a first laser line contour segment across a portion of the mechanical joint;
   measuring a length of second laser line contour segment across a portion of the mechanical joint; and
   comparing through a data processor the first contour segment length and the second contour segment length to a known diameter of the mechanical joint previously stored in a memory device.

6. The method of claim 3 further comprising the step of:
   measuring a height of the mechanical joint through the detected contour.

7. The method of claim 6 further comprising the step of:
   determining the presence of a mechanical joint at the predetermined location through comparing the measured height of the mechanical joint to a predetermined height value stored in a memory device.

8. The method of claim 1 further comprising the step of:
   moving one of the workpiece or the programmable mechanical joint forming device having the sensor to a predetermined nominal positional X,Y location relative to one another where a mechanical joint is to be formed.

9. The method of claim 8 further comprising the step of:
   forming the mechanical joint with the programmable mechanical joint forming device.

10. The method of claim 9 further comprising the steps of:
    prior to forming the mechanical joint, stopping movement of the one of workpiece or mechanical joint forming device along a path of travel at the nominal positional X,Y location of the mechanical joint to be formed;
    calculating whether the determined positional X,Y locational variance is within a predetermined range;
    determining whether the formed mechanical joint is a pass inspection or a fail inspection condition; and
    moving the one of the workpiece or the programmable mechanical joint forming device to the a next predetermined mechanical joint forming nominal X,Y location following a pass inspection condition.

11. A method for inspecting a jointing process, the method comprising the steps of:
    moving one of a workpiece or an automated programmable mechanical joint forming device having a sensor to a predetermined nominal positional location relative to one another where a mechanical joint is to be formed;
    stopping the one of the workpiece or programmable mechanical joint forming device at the predetermined nominal positional location;
    forming the mechanical joint with the joint forming device;
    scanning with the sensor the workpiece in an area including the formed mechanical joint;
    generating surface geometry data of the workpiece in the area including the formed mechanical joint;
    determining from the surface geometry data one of:
       a presence of the formed mechanical joint in the workpiece;
       a positional X,Y location of the formed mechanical joint, or
       a height of the formed mechanical joint relative to the workpiece;
    comparing the determined one of the presence, positional X,Y location or height of the formed mechanical joint to predetermined conditions stored in a memory device;
    determining whether the formed mechanical joint is a pass inspection condition or a failed inspection condition; and
    moving the one of the workpiece or the joint forming device to a next nominal positional location where a next mechanical joint is to be formed on a pass inspection condition of the formed mechanical joint.

12. The method of claim 11 wherein a control loop time includes the time for the scanning the formed mechanical joint, the generating surface geometry data, the comparing the geometry data to predetermined conditions and the determining whether the formed mechanical joint is in the pass or fail inspection condition, the method further comprising the step of:

completing the control loop time in the inspecting a jointing process between 0.1 to 0.65 seconds.

13. The method of claim 11 further comprising the steps of:

storing in a memory device one of the generated surface geometry data or the pass inspection condition or failed inspection condition for each formed and scanned mechanical joint; and correlating the stored one of surface geometry data, pass inspection condition or failed inspection condition to a product including each of the formed and scanned mechanical joints.

14. The method of claim 11 further comprising the step of:

rescanning with the sensor the workpiece in the area of the formed mechanical joint on an inspection fail condition.

15. The method of claim 14 wherein on determining an inspection failure condition a predetermined number of times, the method further comprises the steps of:

a reporting a failure condition; and ceasing further forming of mechanical joints to prevent additional mechanical joint forming failure conditions.

16. The method of claim 11 wherein the step of forming the mechanical joint includes installing a mechanical fastener to connect two layers of sheet material, the mechanical fastener including one of a rivet or a threaded fastener.

\* \* \* \* \*